United States Patent
Madaus et al.

(10) Patent No.: US 10,154,811 B2
(45) Date of Patent: Dec. 18, 2018

(54) DETECTION APPLIANCE AND METHOD FOR OBSERVING SLEEP-RELATED BREATHING DISORDERS

(75) Inventors: Stefan Madaus, Krailling (DE); Caspar Graf von Stauffenberg, Gauting (DE); Harald Vögele, Gauting (DE); Dieter Heidmann, Castle Hill (AU); Dieter Klaus, Maulburg (DE)

(73) Assignee: ResMed R&D Germany GMBH (DE)

( * ) Notice: Subject to any disclaimer, the term of this patent is extended or adjusted under 35 U.S.C. 154(b) by 215 days.

(21) Appl. No.: 10/570,503

(22) PCT Filed: Sep. 3, 2004

(86) PCT No.: PCT/EP2004/009857
§ 371 (c)(1),
(2), (4) Date: Jun. 14, 2006

(87) PCT Pub. No.: WO2005/023109
PCT Pub. Date: Mar. 17, 2005

(65) Prior Publication Data
US 2006/0276718 A1    Dec. 7, 2006

(30) Foreign Application Priority Data

Sep. 3, 2003 (DE) .................................. 103 40 654

(51) Int. Cl.
*A61B 5/08* (2006.01)
*A61B 5/00* (2006.01)
(Continued)

(52) U.S. Cl.
CPC ............ *A61B 5/4818* (2013.01); *A61B 5/087* (2013.01); *A61B 5/113* (2013.01); *A61B 5/1135* (2013.01);
(Continued)

(58) Field of Classification Search
CPC ....... A61M 16/06; A61M 16/00; A61B 5/087; A61B 5/4818; A61B 5/682; A61B 5/6819;
(Continued)

(56) References Cited

U.S. PATENT DOCUMENTS 3,268,845 A * 8/1966 Whitmore ............ A61B 5/1135
338/38
3,483,861 A * 12/1969 Tiep ..................... A61B 5/0803
250/231.1
(Continued)

FOREIGN PATENT DOCUMENTS

DE      101 64 445        7/2003
EP      0 463 620 A1      1/1992
(Continued)

OTHER PUBLICATIONS

International Search Report for PCT/EP04/09857 dated Jan. 21, 2005.
(Continued)

*Primary Examiner* — Christian Jang
*Assistant Examiner* — Karen Toth
(74) *Attorney, Agent, or Firm* — Botos Churchill IP Law LLP

(57) ABSTRACT

A mobile detection appliance and a method for detecting and evaluating a measuring signal that is indicative of the breathing of a sleeping person are used in connection with the observation of sleep-related breathing disorders. Instruments for detecting signals that are indicative of the breathing of a patient are also used. Solutions that enable an especially reliable examination in terms of the occurrence of sleep-related sleeping disorders, especially in the usual surroundings of the person concerned, are provided. The mobile detection appliance includes a sensor device for
(Continued)

Figure 1E:
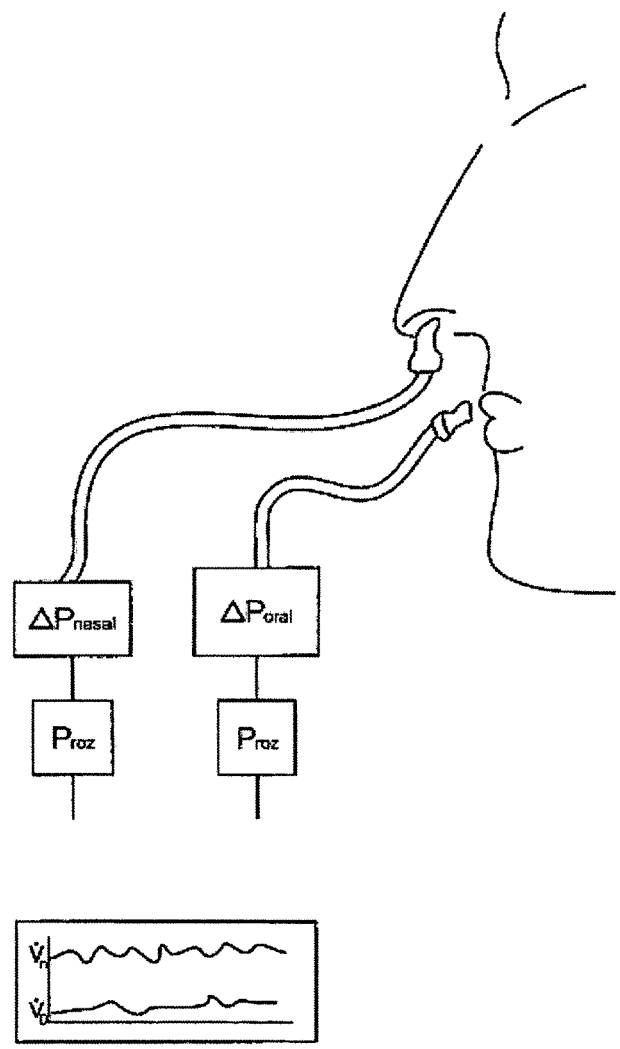

detecting a nasal flow signal that is indicative of a nasal respiratory gas flow, and/or a respiratory flow signal that is indicative of an oral respiratory gas flow, in addition to an electronic data processing unit that includes a memory device and processes the respiratory flow signals that are indicative of the temporal course of the nasal and oral respiration. The data processing device stores data that is indicative of the temporal course of the respiratory flow signals.

32 Claims, 18 Drawing Sheets

(51) Int. Cl.
*A61B 5/113* (2006.01)
*A61B 5/087* (2006.01)

(52) U.S. Cl.
CPC .......... *A61B 5/6825* (2013.01); *A61B 5/6831* (2013.01); *A61B 5/7232* (2013.01)

(58) Field of Classification Search
CPC ... A61B 5/0816; A61B 5/1135; A61B 4/4818; A61B 5/113; A61B 5/6831; A61B 5/08; A61B 5/6823
USPC ........ 600/300, 301, 481, 529, 534, 537, 538
See application file for complete search history.

(56) References Cited

U.S. PATENT DOCUMENTS

| | | | | |
|---|---|---|---|---|
| 4,576,179 A * | 3/1986 | Manus et al. ................. | 600/484 |
| 5,022,402 A * | 6/1991 | Schieberl ............. | A61B 5/0002 |
| | | | 600/484 |
| 5,178,151 A * | 1/1993 | Sackner ............... | A61B 5/1135 |
| | | | 600/485 |
| 5,197,489 A * | 3/1993 | Conlan ......................... | 600/595 |
| 5,277,194 A * | 1/1994 | Hosterman .......... | A61B 5/1135 |
| | | | 600/534 |
| 5,400,012 A * | 3/1995 | Walton ................. | A61B 5/1135 |
| | | | 340/573.1 |
| 5,423,328 A * | 6/1995 | Gavish ................. | A61B 5/1135 |
| | | | 600/534 |
| 5,454,376 A * | 10/1995 | Stephens .............. | A61B 5/1135 |
| | | | 600/534 |
| 5,458,137 A | 10/1995 | Burk et al. | |
| 6,090,037 A * | 7/2000 | Gavish ................. | A61B 5/1135 |
| | | | 600/27 |
| 6,599,242 B1 * | 7/2003 | Splett et al. ................... | 600/300 |
| 6,752,766 B2 * | 6/2004 | Kowallik et al. ............. | 600/538 |
| 7,089,936 B2 * | 8/2006 | Madaus ............ | A61M 16/0051 |
| | | | 128/204.18 |
| 2002/0029004 A1* | 3/2002 | Starr et al. ..................... | 600/538 |
| 2002/0123692 A1* | 9/2002 | Pail ...................... | A61B 5/1135 |
| | | | 600/534 |
| 2002/0133061 A1* | 9/2002 | Manetta ......................... | 600/300 |
| 2003/0100843 A1* | 5/2003 | Hoffman .............. | A61B 5/0809 |
| | | | 600/538 |
| 2003/0139780 A1* | 7/2003 | Markowitz et al. ............ | 607/17 |
| 2003/0206116 A1* | 11/2003 | Weiner et al. ........... | 340/870.28 |
| 2004/0107373 A1* | 6/2004 | Ferrara ......................... | 713/300 |
| 2006/0129055 A1* | 6/2006 | Orr et al. ....................... | 600/532 |

FOREIGN PATENT DOCUMENTS

| | | | | |
|---|---|---|---|---|
| WO | WO 93/09834 | | 5/1993 | |
| WO | 00/33735 A1 | | 6/2000 | |
| WO | WO 00/61000 A1 | | 10/2000 | |
| WO | WO 01/28416 A1 | | 4/2001 | |
| WO | 02/00283 A1 | | 1/2002 | |
| WO | WO 02/22017 | | 3/2002 | |
| WO | 02/082997 A2 | | 10/2002 | |
| WO | WO 03/061471 | | 7/2003 | |
| WO | WO 2004/066804 | * | 8/2004 | |
| WO | WO 2006/133548 | * | 12/2006 | ............... A61B 5/04 |

OTHER PUBLICATIONS

Office Action dated Oct. 23, 2013 in German Application No. 10 2004 042 797.6, with English translation (22 pages).
Search Report dated Mar. 9, 2015 issued in corresponding EP Application No. 14 19 3694.8 (6 pages).

* cited by examiner

Fig. 1a
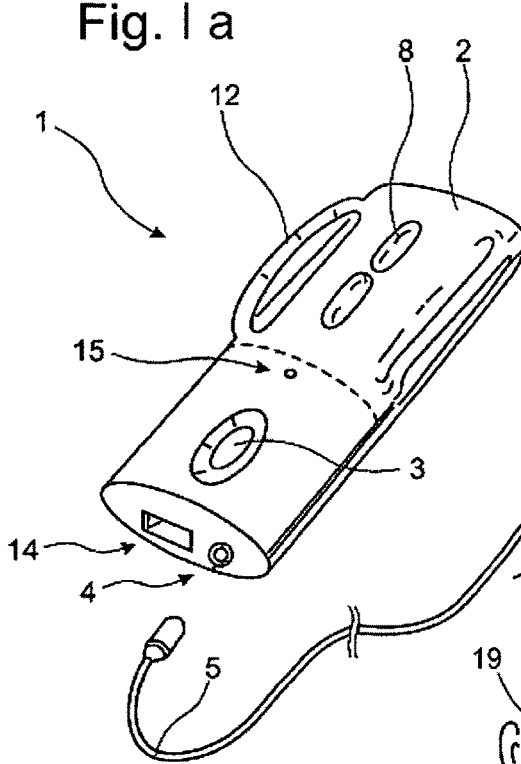
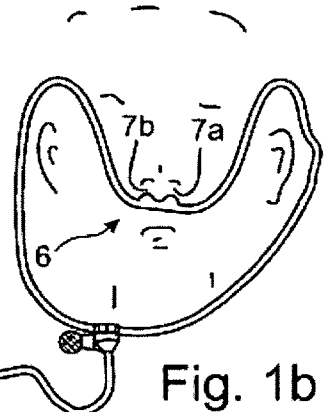
Fig. 1b
Fig. 1c
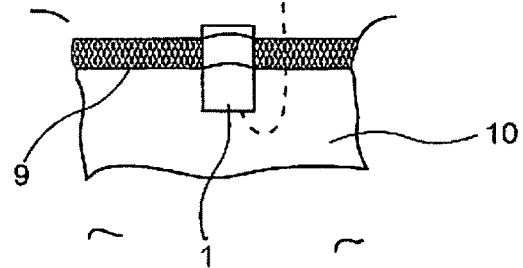
Fig. 1d

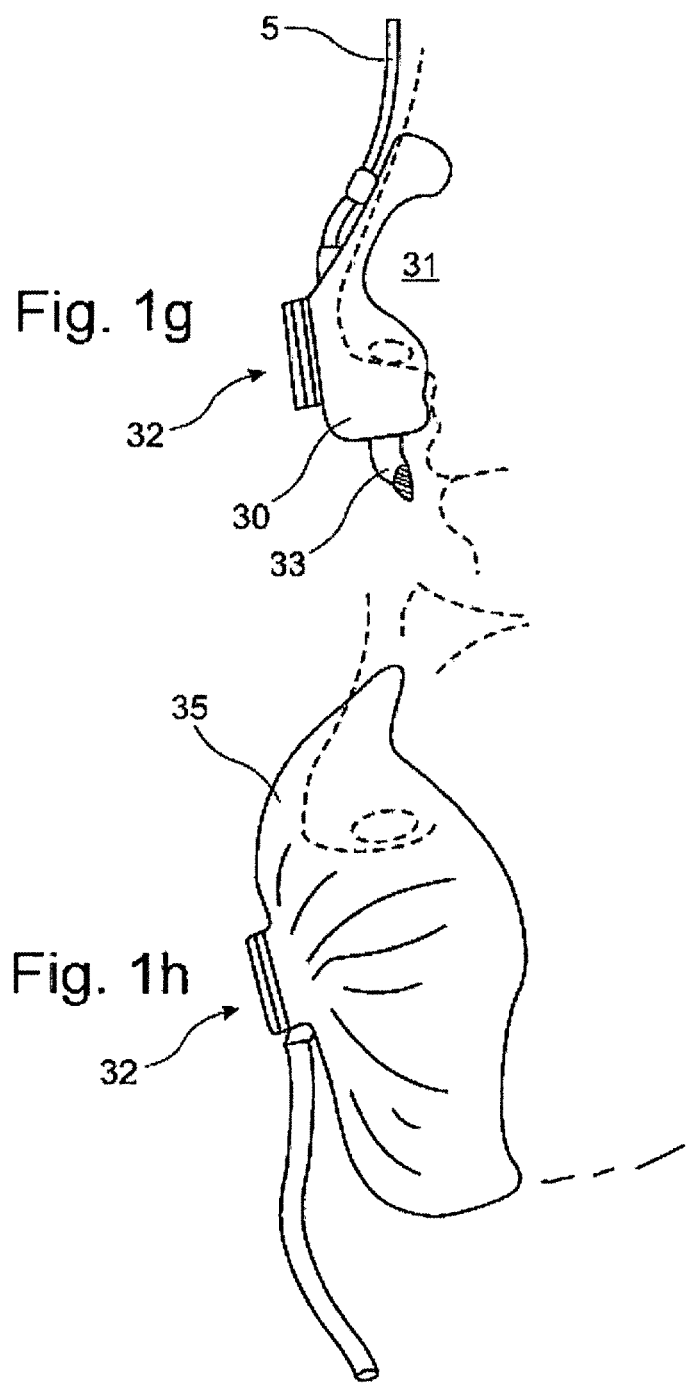

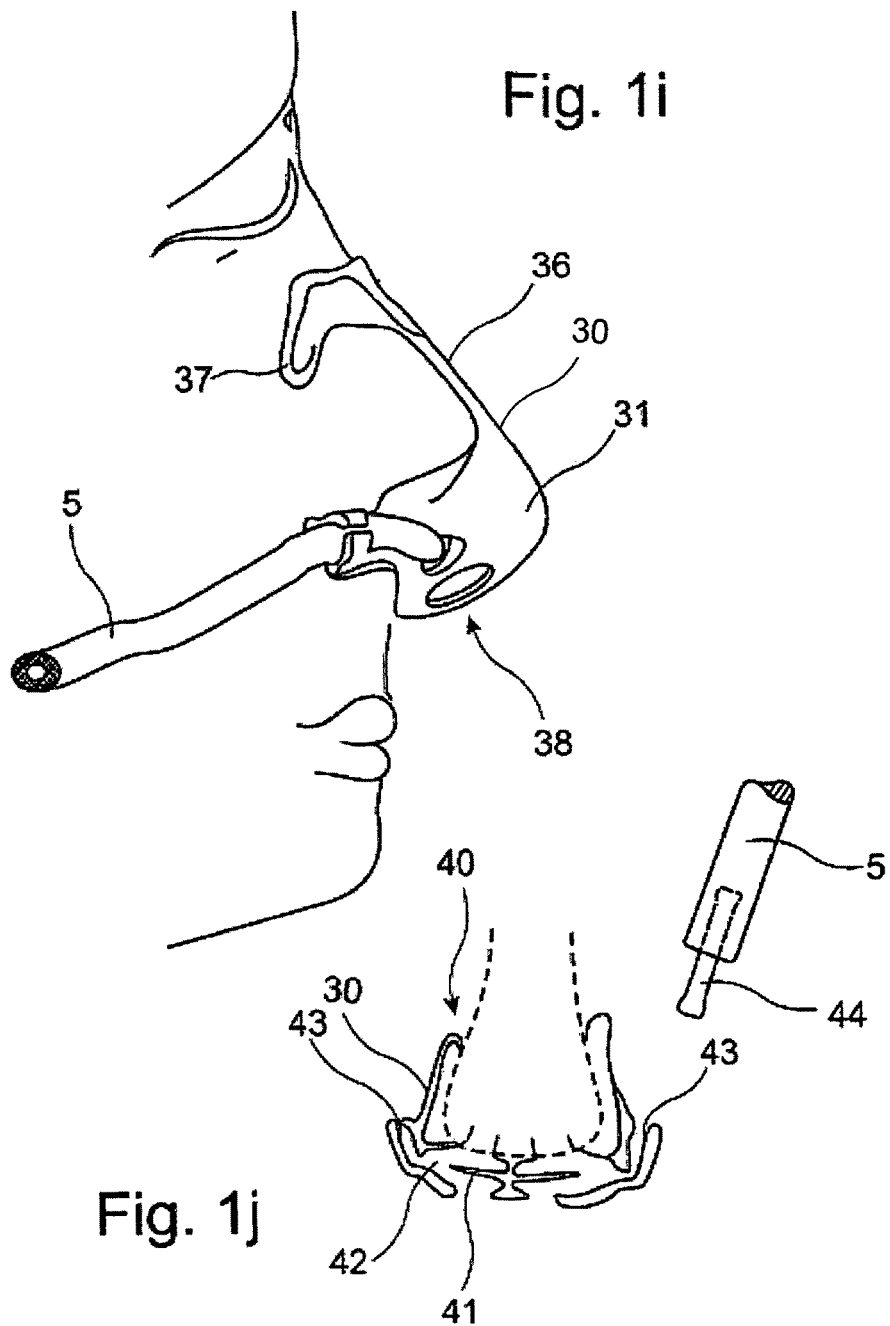

Apnea

Characteristic:

A breathing cessation lasting longer than 10 seconds.

Example:

Hypopnea

Characteristic:

Three normal breaths are followed by at least two, but at most three large breaths. A differential volume (AV) appears in this case Example:

Flow limitation:

Characteristic:

A limitation during inspiration is apparent in the breathing. A plateau, or several plateaus are formed.

Example:

Stable respiration:

Characteristic:
The respiratory flow, i.e. the frequency, amplitude and pattern of the breathing is regular during a given time period.

Unstable respiration:

Characteristic:
The breathing stability is < 0.8 because the respiratory flow is irregular. Respiratory disturbances are occurring.
Example:

Expiratory and inspiratory snoring:

Characteristic:
High frequency oscillations arise on the pressure signal.
A temporal association of the snoring to the respiratory
flow can be established.
Example:

DETECTION APPLIANCE AND METHOD FOR OBSERVING SLEEP-RELATED BREATHING DISORDERS

This application is the US national phase of international application PCT/EP2004/009857 filed 3 Sep. 2004, which designated the U.S. and claims priority to DE 103 40 654.9 filed 3 Sep. 2003, the entire contents of each of which are hereby incorporated by reference.

The invention relates to a detection appliance and a method for acquiring and evaluating a measuring signal that is indicative of the breathing of a sleeping person, in connection with the observation of sleep-related breathing disorders. The invention also relates to instruments for acquiring signals that are indicative of the breathing of a patient.

For the purposes of investigating sleep-related breathing disorders, so-called polysomnograph devices are known which typically possess multiple measurement channels for acquiring measurement signals relating to physiological state indicators for the patient. As can be seen in the patent application DE 101 64 445.0 originating from the present applicant, the acquisition of ECG and blood pressure signals for the purposes of diagnosing a patient with regard to his/her breathing characteristics during a sleeping phase, and the recording of these signals together with signals that describe the breathing activity of the patient, is known. These signals describing the breathing activity of the patient can be generated by means of so-called thermistors or pneumotachographs. The acquired signals can be visualized in temporal relationship to one another and evaluated as part of a review by a medical specialist. Based on the medical specialist's evaluation, it is possible to determine whether any respiratory disorders that may be present can be prevented by the supply of respiratory gas at an elevated pressure (CPAP therapy). Suitable therapy parameters can also be determined as part of the review by a medical specialist.

When investigating persons with signs of sleep-related respiratory disorders, examination of the generated measurement signals can, in practice, lead to different findings in some circumstances, in particular in regard to the type and severity of obstruction-related impairment of the respiratory passages and in regard to the evaluation of the general physiological state of the patient. When an evaluation of the symptoms is inadequate, the problem arises that a therapy need that may exist is not recognized, or therapy parameters are selected that do not adequately take into consideration the actual physiological requirements, or at least limit the comfort of the therapy.

The decision by the affected person to submit to an investigation of possible sleep-related respiratory disorders in a sleep laboratory is often not taken until the secondary symptoms of the OSA disorder are already significantly impacting on how the disorder is experienced. The burden that OSA places on the affected person when already in an advanced stage makes a precise diagnosis of the illness more difficult.

The aim of the invention is to provide solutions that enable an especially reliable investigation into the occurrence of sleep-related breathing disorders, in particular in the usual surroundings of the person concerned.

To this end, in a first form of embodiment, a mobile detection appliance is provided, said appliance comprising a sensor device for acquiring a nasal flow signal that is indicative of a nasal respiratory gas flow, and/or a respiratory flow signal that is indicative of an oral respiratory gas flow, in addition to an electronic data processing unit which comprises a memory device and is used to process the respiratory flow signals that are indicative of the temporal course of the nasal and oral respiration, said data processing device being configured in such a way that it stores data that is indicative of the temporal course of the respiratory flow signals.

This provides an advantageous means, via a detection appliance suitable for self-application in the home area, i.e. in the familiar surroundings of the affected person, of detecting characteristic features of breathing during the sleep phase in a manner that enables the physiological state of the affected person to be determined with an especially high degree of reliability. In can then be assessed on the basis of a standardized, computer-based analysis of the measurement results whether, and if so in what severity OSA symptoms are present, and whether a more in-depth examination by means of a sleep laboratory should be recommended.

The data processing unit, or a signal transmission circuit preceding it, is in preference configured in such a way that it is possible to test whether a given acquired respiratory flow signal fulfils prescribed signal quality criteria. Should the acquired signal not fulfil certain criteria, it is possible to suppress the recording of the signal, or recording entries that indicate the temporal locations of signals that were classified as invalid.

The data processing unit is in preference designed in such a way that it has access to a time-keeping device so that the data that is indicative of the respective respiratory gas flow can be recorded in conjunction with time information.

The data processing unit is in preference implemented in conjunction with a data compression system enabling the acquired time-dependent signals to be recorded in compressed form.

The data processing unit is also in preference configured in such as way that the recording process is initiated by a switching impulse initiated by the user. It is possible to make the generation of the switching impulse conditional upon the pressing of a switch button for a prescribed minimum duration of, for example, 3 seconds.

The data processing unit can be configured in such a way that it stores the data when the acquired respiratory flow signals fulfil a certain criterion, for example a prescribed periodicity criterion.

The detection appliance comprises in preference a pressure measurement connection to which can be connected a measurement cannula, a pair of measurement cannulae, or a bundle of measurement cannulae. The first measurement cannula can be connected to a nasal pressure measurement spectacle facility for acquiring a back-pressure signal obtained from the respiratory gas flow out of the nasal openings. The second measurement cannula can be connected to the user in such a way that it can be used to collect a signal indicative of the gas flow via the mouth of the user, if present.

It is possible to equip the detection appliance with a second pressure measurement connection, also intended for detecting nasal respiration, in order to acquire a second nasal respiration flow signal. The ability to acquire two pressure measurement signals makes it possible to operate the detection appliance in such a way that it can separately acquire the respiratory flow signals from each of the left and right nasal openings respectively.

The detection appliance comprises in preference a facility to detect chest expansion. The facility for detecting the chest expansion may comprise a strap element that can be fitted around the chest area of the user. It is possible to design this strap element in such a way that a signal that is indicative of the extension of the strap, or the load on the strap can be derived (e.g. changes in the electrical resistance of an embedded conductor). It is also possible to provide the detection appliance with a means of detecting the load on the strap. In particular, it is possible to provide the detection appliance with a loop feature by means of which the extension of the strap, or the forces on the strap can be acquired. It is also possible to provide the detection appliance with pressure or force detection structures by means of which the force exerted by a strap located on top of these force detection structures can be acquired. The strap for detecting the chest expansion can also serve to fasten the detection appliance to the user.

The recording process can, in preference, be ended by means of a switching signal triggered by the user. This switching signal can in particular be generated by the switch, in particular a press button, previously used to switch on the appliance. It is also possible to configure the detection appliance in such a way that the recording process can be ended as a result of the fulfilment of a time criterion. In particular, it is possible to end the recording process when it has reached a prescribed duration of, for example, 9.5 h.

It is also possible to end the recording process under switch control if the acquired respiratory flow signal fulfils a certain switch-off criterion within a certain switch-off time window. It is possible to limit the recording capacity to a specific number of recordings, in particular to two recordings.

According to a special form of embodiment of the present invention, the detection appliance can be provided with an interface device for transmitting the recorded data to an external analysis system. This interface device is in preference provided in the form of a USB interface or an infrared interface.

It is also possible, in an especially advantageous manner, to design the detection appliance in such a way that the memory device incorporated in the recording device is removable. Such a memory device can be in the form of a card or, in particular, a USB flash stick. By first creating an entry in the memory device, it is possible to record personal data on the storage medium. On the basis of this initial recording, it is possible to pre-configure the detection appliance or to ensure that the acquired data is correctly assigned to the specific user.

The configuration of the data processing unit is in preference set by a data processing program, where this data processing program is in preference modifiable or substitutable. The reproduction of the data processing program in the detection appliance can occur via the previously mentioned interface device, additional interface devices or the storage medium.

Along with an in preference intuitive and easy-to-use switch device, the detection appliance is also provided with indicator devices for indicating the operational readiness or the functional state of the detection appliance. It is possible to signify the recording readiness of the detection appliance by the periodic blinking of a signal diode.

The detection appliance comprises in preference a power supplying device which may, for example, take the form of a battery unit. The battery unit is in preference as compact as possible so that the detection appliance can be designed to be flat and miniature and possess little weight.

The data processing unit is in preference coupled to a calibration device for calibrating the respiratory flow signal. The calibration device can be designed in such a way that it can perform an automatic adjustment of the system to the acquired signal level.

According to a special form of embodiment of the present invention, the detection appliance is built in such a way as to feature a structural component that is compatible with a playback unit the construction of which corresponds to that of a Game Boy.

It is possible to design the detection appliance in such a way that at least one portion of it can be introduced into the insertion slot of a Game Boy.

According to a special form of embodiment of the present invention, the detection appliance is designed in such a way as to comprise a base module to which can be coupled a recording transfer module.

The detection appliance is in preference designed with such a Game Boy compatible structure. This enables the recorded data to be visualized via an intuitive, simply-to understand user interface on a conventional end-user device and, if necessary, to be processed with regard to selected properties.

The supply of power and the conversion of the pressure signal occurs in preference in the base module. To this end, the base module comprises in preference a battery compartment and a pressure sensor.

The recording module comprises in preference a data processing unit that is configured in such a way that it records onto a memory device data that is indicative of the temporal course of the breathing. The recording module can be provided with an interface device for reading the recorded data. It is possible to connect the memory device to the recording module in a detachable manner so that is possible to separate the memory device from the recording module and introduce it into another system for further evaluation and visualization.

The acquisition of the respiratory signal can, as an alternative to acquisition using a nasal cannulation arrangement, also occur by means of other measuring equipment.

According to the invention, the initially stated aim can be solved by means of a method for the provision of an evaluation result that is indicative of the physiological state of a person and is based on measurement signals associated with the breathing of that person, where evaluation characteristics are generated from said measurement signals through the use of several analysis systems and a least one evaluation result is generated from a result generation step based thereon in which the evaluation characteristics are subjected to an associative analysis, whereby said measurement signals are recorded by a mobile detection appliance applied by the affected person in the course of a signal acquisition phase preceding the analysis.

This provides an advantageous means of creating a quantity of data from the signal collection carried out at home by the user over a continuous period of approx. 6 to 8 hours based on which evaluation characteristics can be generated from which can be obtained reliable evaluation results obtained in a standardized repeatable manner that can in an advantageous manner form the basis of a subsequent diagnosis and thereby facilitate a standardized preliminary evaluation.

The associative analysis of the respiratory properties determined for the individual breaths can cover a time frame that spans, for example, a prescribed number of breaths, e.g. 30, or an adaptively optimised number of breaths. It is also possible, in particular for the purposes of assessing the physiological state of the user, for example as the basis for a medical diagnosis, to perform certain correlation operations over a time window spanning sleep phase related periods, selected time segments or the entire measurement period. According to an especially advantageous embodiment of the invention, correlation operations are used to select raw data and/or intermediate results that allow characteristic values, in particular indices, to be generated in an especially reliable manner.

According to an especially advantageous embodiment of the invention, the associative analysis forms the basis of a physiological characterization of the symptoms that may be present in the person being examined.

According to an especially advantageous embodiment of the invention, the evaluation characteristics are generated on the basis of correlation criteria, in particular statistical analysis systems, that allow, for example, commonalities with preceding breaths, or in preference adaptively optimised reference criteria, e.g. of reference breaths, to be evaluated. The correlation criteria can, in particular, be applied to the first and/or second derivative of the acquired respiratory gas flow. The generation of the characteristic features of each breath can occur with the aid of statistical methods. The associative analysis of the properties determined for each breath can also occur with the aid of statistical methods.

Using the evaluation characteristics generated for each breath or specific breath sequences, a feature array can be progressively filled that describes a time window, at least for selected evaluation characteristics, that is at least as big as the smallest time window used in the associative analysis of the evaluation characteristics.

According to a particularly advantageous embodiment of the invention, the evaluation characteristics are generated in such a way that they include, for example, evaluation characteristics that provide information about the duration of a breath and/or, for example, characteristic information about what can be considered normal breathing. Based on these evaluation characteristics, it is possible to determine as part of the associative analysis the duration of periods of normal breathing.

Furthermore, the evaluation characteristics are by advantageous means generated in such a way that they contain information about the occurrence of any flow limitation features in the individual breaths or, in preference, also certain representative information relating to flow limitations. Based on an associate analysis of the evaluation characteristics obtained for these flow-limited breaths, it is possible to describe the duration of certain properties of the, at least in part, flow-limited breathing sequences.

Evaluation characteristics can also be generated for periods in which no breathing activity was registered, and these can be used to determine the length of any apnoea sequence phases and/or generate characteristic features for the properties of these apnoea phases as part of an associative analysis. These evaluation characteristics include, in preference, information about the type of the apnoea phases, e.g. whether the apnoea phase can be classified as central, obstructive or a combination of these (mixed apnoea phase).

According to an especially advantageous embodiment of the invention, such evaluation characteristics are also generated for snoring phases, phases with Cheyne-Stokes breathing and hypoventilation phases.

The evaluation characteristics also include in preference data or information from which the body position, the head position and, in preference, also the degree of rotation of the neck can be derived. The evaluation characteristics may already contain data indicative of the sleep phases.

The generated evaluation characteristics are in preference saved with reference to a given recorded breath or taking into account their time location. That is, the generated evaluation characteristics can be associated with a defined time window—or the associated breath in the case of normal breathing.

It is also possible, as part of the associative analysis, to generate a snoring index.

It is also possible, as part of the associative analysis, to generate a sleeping phase index. In conjunction with the respiratory phase analysis, it is possible to distinguish between inspiratory (relevant to obstruction) and expiratory (less relevant) snoring. It is also possible, as part of the associative analysis, to generate a periodic respiration index. It is also possible, as part of the associative analysis, to generate a respiration volume index.

The respiratory gas flow can be measured either at ambient pressure or under a defined modified respiratory gas pressure.

In preference, at least some of the evaluation characteristics are generated by considering the first and second derivative of the temporal course of the respiratory gas flow.

According to a further form of the present invention, the initially stated aim is also solved by means of an appliance for carrying out the previously described method, said appliance comprising a measurement signal input device and a computing device for the provision of several analysis systems, where the analysis systems are used to generate evaluation characteristics from said measurement signals and at least one evaluation result is generated from a result generation step based thereon, and where the computing device is configured in such a way as to subject the evaluation characteristics to an associative analysis.

In the course of detecting the respiratory activity of the user on the basis of data that is indicative of the respiratory gas volumetric flow rate, it is possible to recognize actual individual breaths. The beginning and end of the inspiration and expiration phase of a breath can, for example, be determined in conjunction with an examination of the first and second derivative of the respiratory gas flow signal along with consideration of the likely tidal volume. Based on the evaluation results, it is possible to determine the duration of the breath phases, the actual volume of each breath and the breathing pattern.

The physiological state of the person under examination can also be determined through statistical analysis of the properties of several successive breaths. A reduction in raw data can be achieved on the basis of an extraction of the characteristics of each individual breath. Based on the statistical analysis of the properties of several successive breaths, it is possible to differentiate between obstruction-related snoring and non-obstruction-related snoring. This enables oscillation properties associated with snoring events to be characterized without the need for a microphone device.

The occurrence of any snoring-related oscillations can be detected on the basis of the temporal course of the respiratory signal. It is therefore possible, for example, to extract the pressure oscillations caused by snoring from the signals generated by suitable pressure sensing devices. In particular, it is possible to classify snoring events according to their point of origin (soft palate, larynx . . . ) on the basis of a frequency and amplitude analysis, e.g. Fast Fourier analysis.

Based on an associative analysis of the evaluation characteristics, the following obstructive sleep disorders (OSA) in particular can be recognized:

Apnoea, hypopnea, flow-limited breathing, and stable and unstable breathing.

A respiratory disorder is classified as an apnoea event if a breathing cessation is detected the duration of which exceeds a predefined period of, for example, 10 seconds.

A hypopnea event can be considered to be present if, for example, it is identified that three breaths that have been classified as normal are followed by at least two but at most three larger breaths. A further criterion that can be used is the difference in inspiratory volume of the breaths under consideration.

A flow limitation can be identified in a particular breath being examined if the respiratory gas flow exhibits certain plateau zones or multiple maxima during the inspiratory phase.

Any high frequency oscillations evident in a pressure signal can, in conjunction with the respiratory flow signal, be classified as inspiratory or expiratory snoring. The generated evaluation characteristics with regard to the occurrence of snoring can be used as input for the associative analysis used to generate the evaluation results.

The inventive acquisition and evaluation of signals that are indicative of the respiratory gas flow can provide information for describing and visualizing the physiological state of a person, in particular with regard to an illness connected with sleep-related respiratory disorders. The inventive signal acquisition and evaluation can be used to configure respiratory devices.

In a particular form of embodiment of the invention, at least two of the following are applied in combination:

The degree of statistical certainty of the evaluation or classification results obtained is determined.

For each breath, breath-specific characteristics are determined on the basis of defined analysis procedures.

These analysis procedures specifically consider the inspiratory process, the expiratory process, the transition between the aforementioned processes, the properties of the respiratory gas flow vs time curve within each breathing cycle, combinatorial analysis of the characteristics of the temporal course of the respiratory gas flow within a given breath.

The commonalities between breaths is determined.

Differences or temporal changes in the breath characteristics are determined and taken into consideration when assessing the physiological state of the user.

Based on a multi-variate analysis of individual characteristics, evaluation results are generated that describe the physiological state or physiological properties in a standardized parametric manner.

Figure 1F:
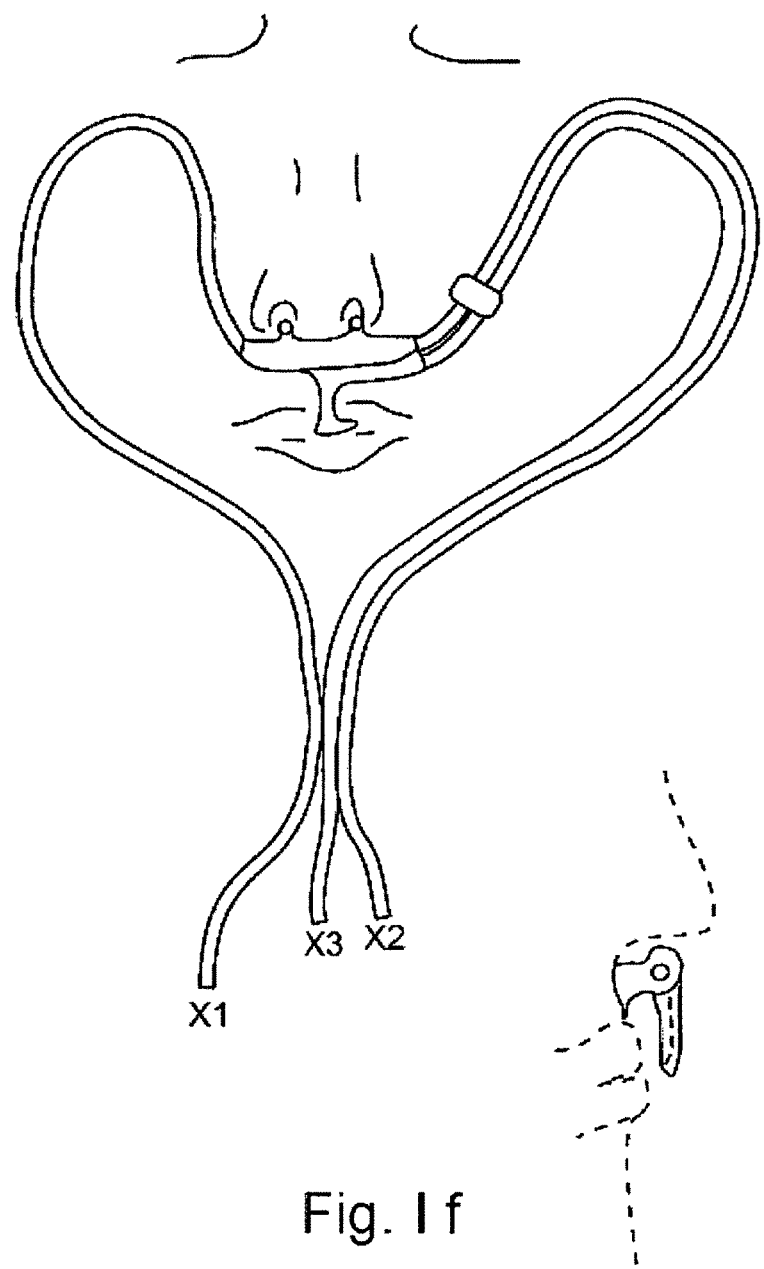
Figure 1K:
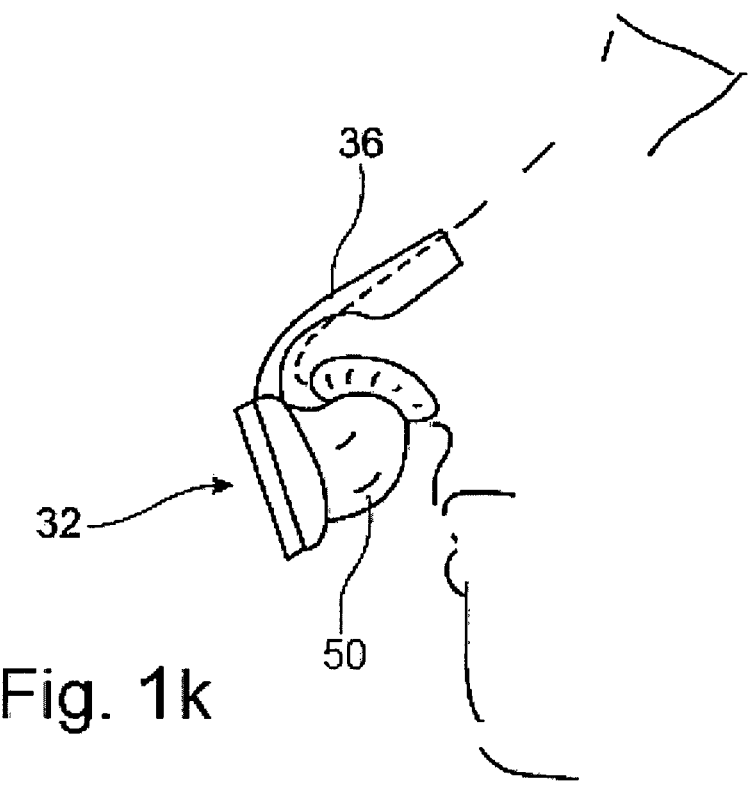
Figure 1L:
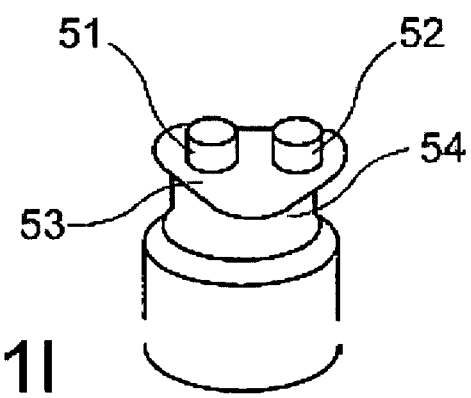
Figure 1M:
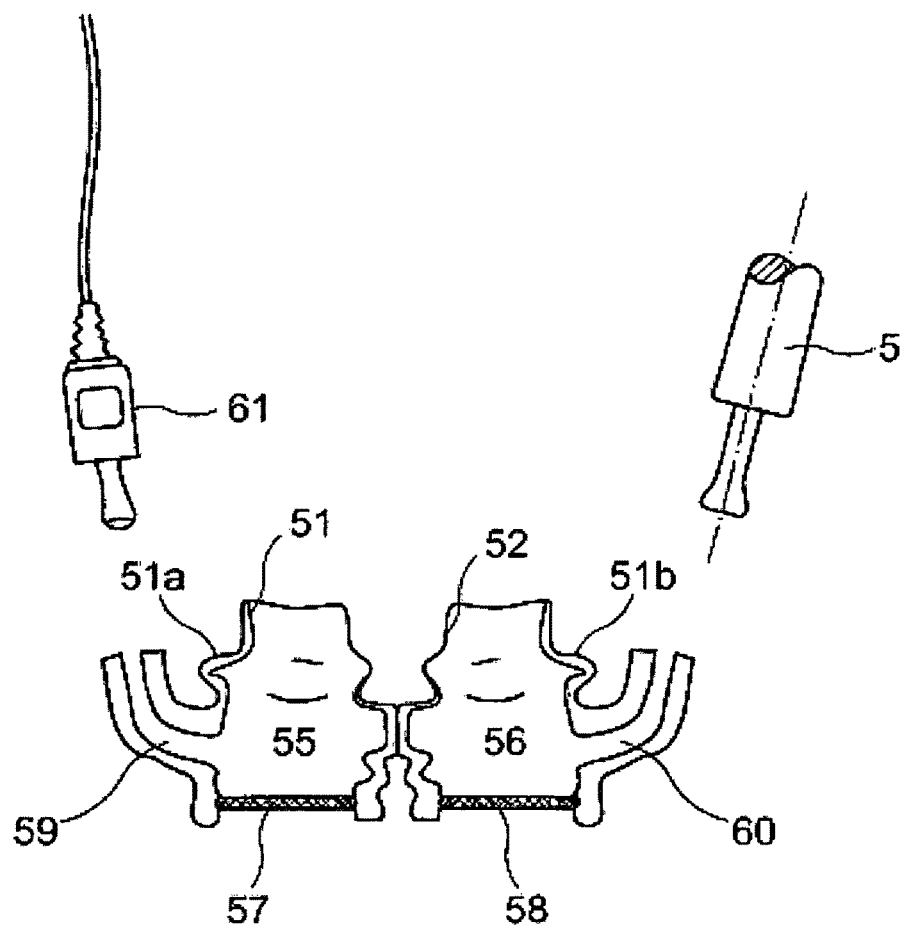
Figure 1N:
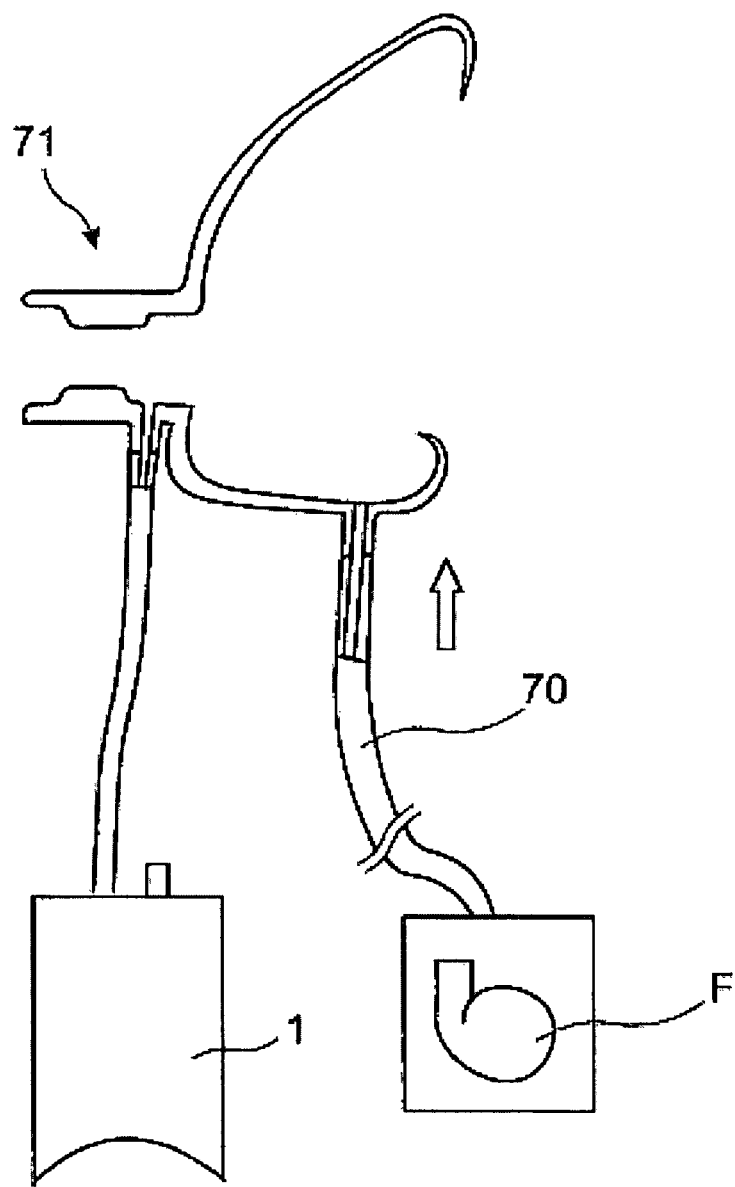
Figure 2:
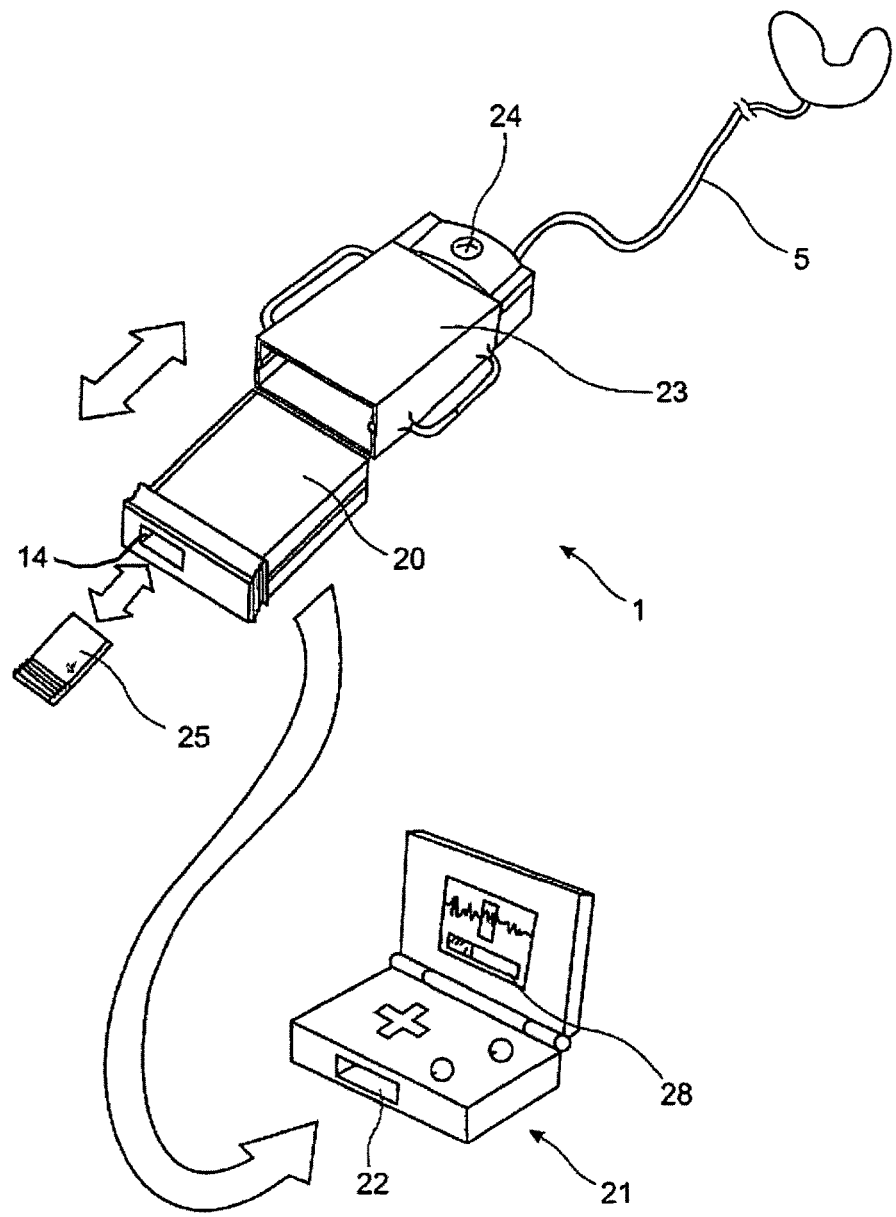
Figure 3:
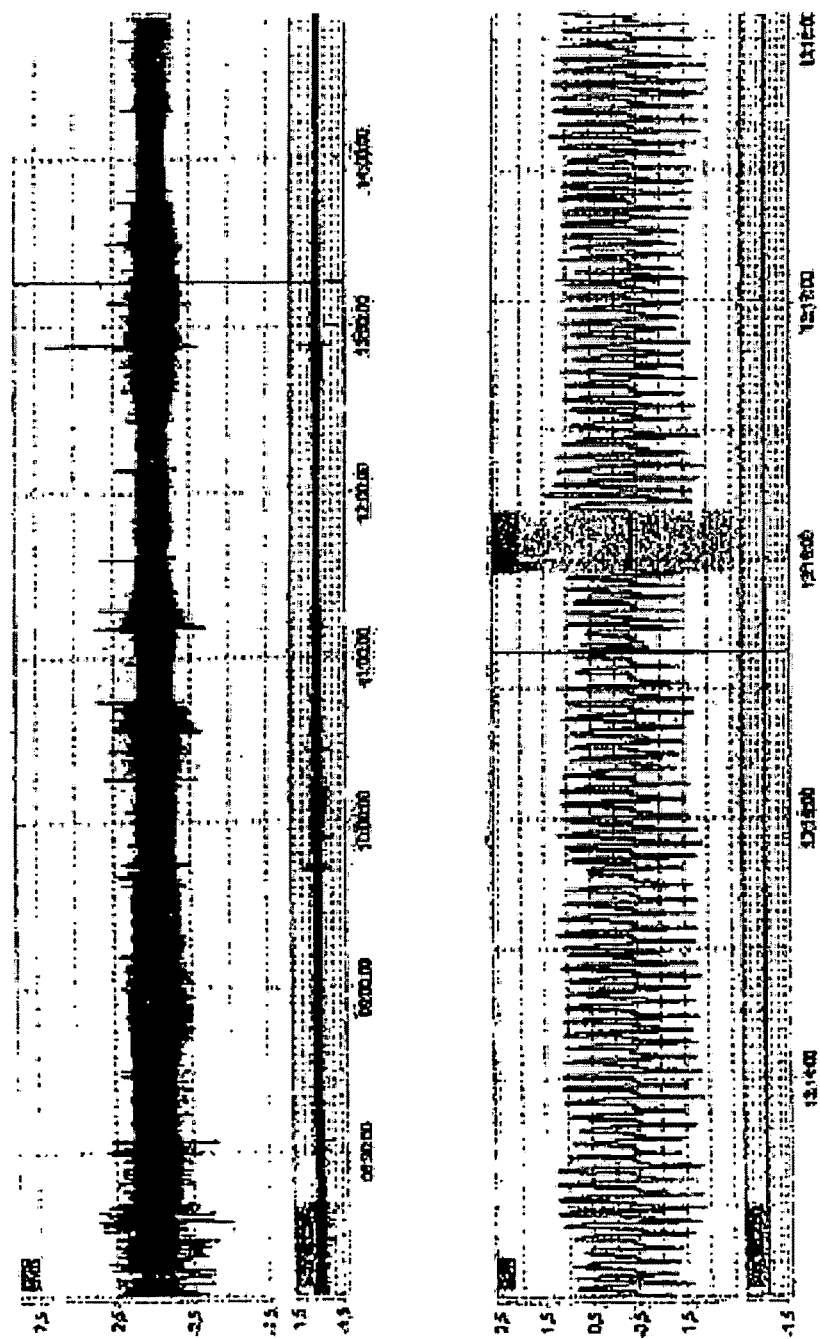
Figure 4A:
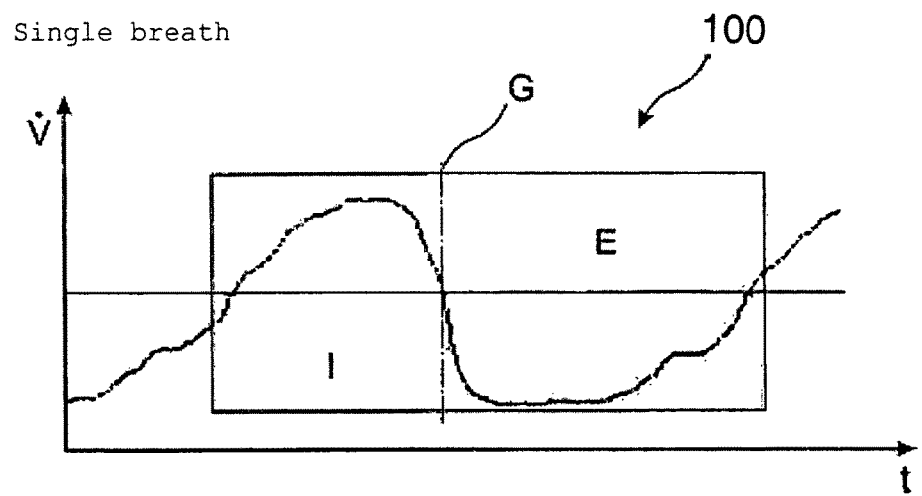
Figure 4B:
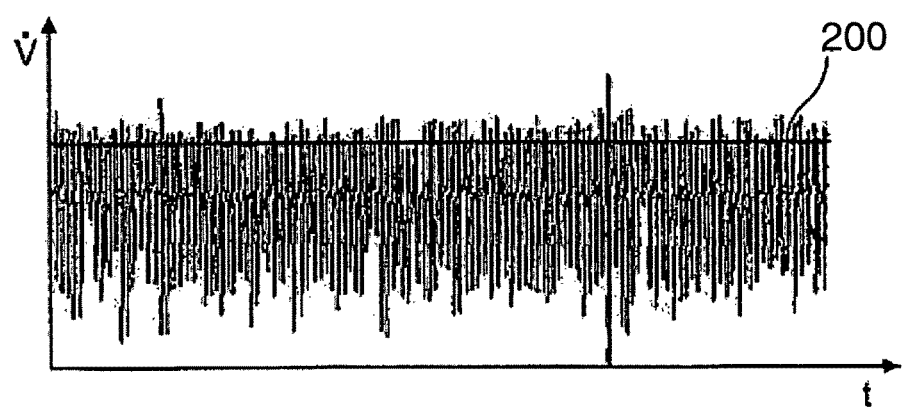
Figure 4C:
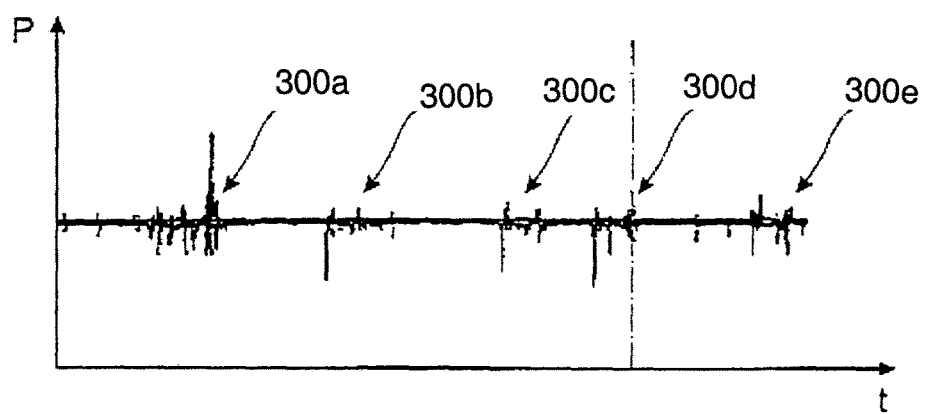
Figure 4D:
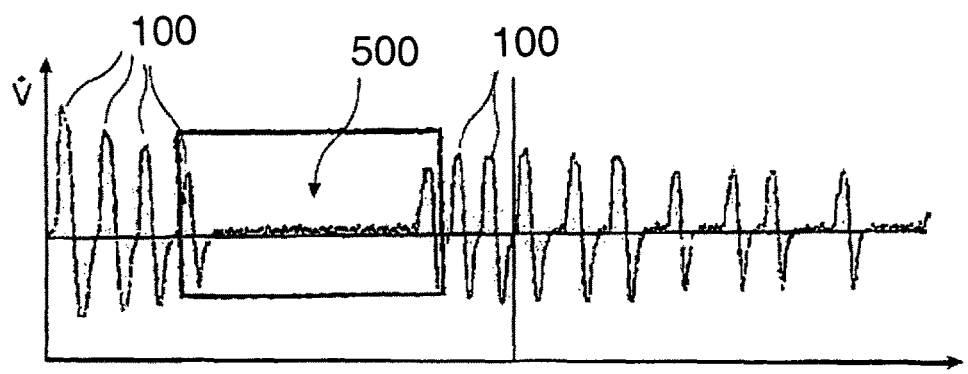
Figure 5:
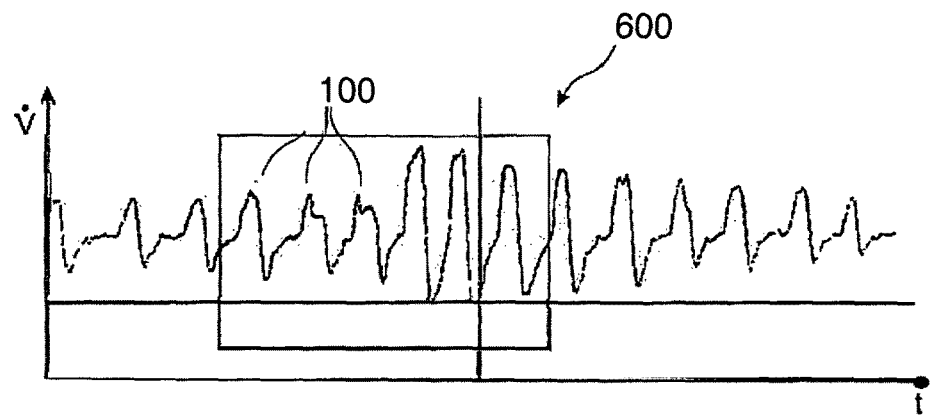
Figure 6:
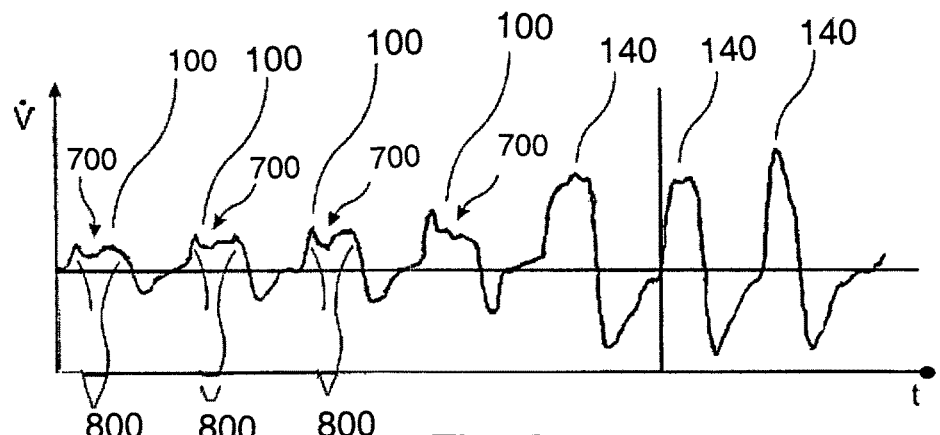
Figure 7:
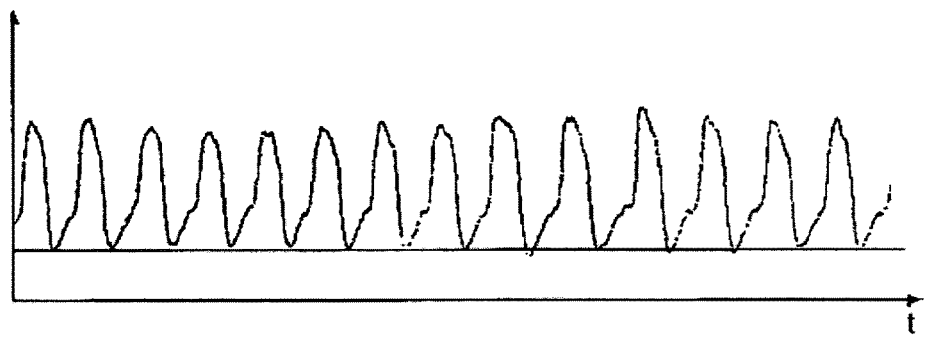
Figure 8:
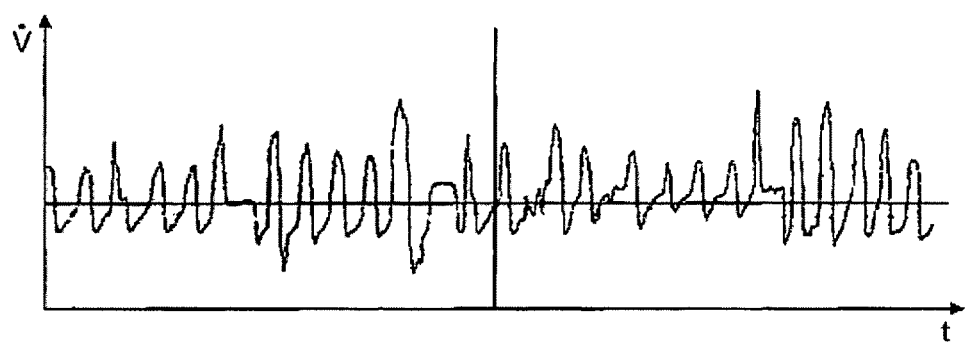
Figure 9:
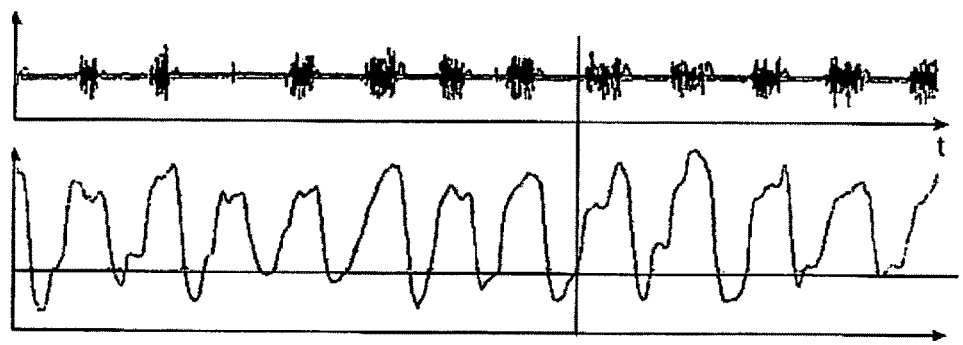

Further particulars and characteristics of the invention can be found in the following description in conjunction with the drawings. They show:

FIG. 1a a perspective view of a first embodiment of the inventive detection appliance;

FIG. 1b a sketch illustrating a nasal cannulation arrangement for detecting the respiratory gas flow by means of back-pressure measurement in the region of the nasal openings;

FIG. 1c a sketch illustrating a cannulation arrangement for detecting the respiratory gas flow by means of pressure measurement in the interior of a one-way filter mask;

FIG. 1d a sketch illustrating a means of attaching the detection appliance to the user with the aid of a strap fitted around the chest;

FIG. 1e a sketch illustrating a second embodiment of the inventive detection appliance with several connection segments used to connect pressure measurement cannulae for the separate detection of nasal and oral respiration;

FIG. 1f a sketch illustrating a concept for monitoring respiration by measuring signals that are indicative of the respiratory gas flow through the left nasal opening, the right nasal opening and the mouth of the user;

FIG. 1g a sketch illustrating a nasal spectacle arrangement with integrated cannula for detecting oral respiration;

FIG. 1h a sketch illustrating a concept for monitoring respiration by taking measurements with the aid of a full-face mask;

FIG. 1i a sketch illustrating an acquisition device intended for application to the nose of the user;

FIG. 1j a sketch illustrating a flow path design suitable for the acquisition device according to FIG. 1i;

FIG. 1k a sketch illustrating an acquisition device intended for nasal application which covers the nasal openings of the user;

FIG. 1l a sketch illustrating an acquisition device intended for attachment to the nasal opening area;

FIG. 1m a sketch illustrating another acquisition device intended for attachment to the nasal opening area with diaphragm or flap windows;

FIG. 1n a sketch illustrating a measurement concept with active supply of purging air;

FIG. 2 a sketch illustrating a detection appliance of modular design with a Game Boy compatible base module;

FIG. 3 a screenshot illustrating a possible method of displaying the measurement data collected by the inventive means using an evaluation device in the form of a computer, e.g. a notebook or Game Boy;

FIG. 4a a diagram illustrating the respiratory gas flow for a single breath;

FIG. 4b a diagram describing the temporal course of the respiratory gas flow over a number of breaths;

FIG. 4c a diagram depicting the temporal course of the respiratory gas pressure with individual pressure oscillations caused by snoring;

FIG. 4d a diagram depicting the temporal course of the respiratory gas flow over a number of breaths interrupted by an apneic period;

FIG. 5 a diagram describing the temporal course of the respiratory gas flow with a hypopnea event;

FIG. 6 a diagram of the temporal course of the respiratory gas flow over a number of breaths, several of which are flow-limited;

FIG. 7 a diagram illustrating the temporal course of the respiratory gas flow in the case of a, for the most part, unimpaired stable respiration;

FIG. 8 a diagram illustrating the temporal course of the respiratory gas flow in the case of an unstable, impaired respiration;

FIG. 9 a diagram depicting the temporal course of the respiratory gas flow in which pressure signal oscillations caused by snoring are evident;

FIG. 1a shows an inventive mobile detection appliance 1 featuring a housing unit 2 into which is incorporated a pressure sensor, not shown in detail here, that is used to acquire and generate a respiratory flow signal that is indicative of the respiratory gas flow. The detection appliance 1 also comprises an electronic data processing unit incorporating a memory device for processing the respiratory flow signal indicative of the temporal course of the respiratory flow. The processing unit is configured in such a way that it stores data that is indicative of the temporal course of the respiratory flow signal.

The detection appliance 1 shown is particularly suitable for use in the home, i.e. in the familiar surroundings of the affected person for the purposes of recording features characteristic of the respiration during the sleep phase in such a way that it enables the physiological state of the affected person to be evaluated in an adequately informative and standardized manner. On the basis of a standardized analysis of the measurement results obtained, an assessment can be made as whether, and if so to what degree, symptoms of OSA are present and whether a more in-depth investigation in a sleep laboratory should be recommended.

The data processing unit is configured in such a way that it checks whether the acquired respiratory flow signal fulfils prescribed signal quality criteria. In the event that the acquired signal does not fulfil certain criteria, signal recording is suppressed and a data entry is performed that indicates the time locations of periods with signals that were classified as invalid.

The data processing unit is designed in such a way that it has access to a time-keeping device so that the data indicative of the respiratory flow signal can be recorded in conjunction with time information.

The data compression system implemented in conjunction with the data processing unit allows the acquired time-dependent signals to be recorded in compressed form.

The data processing unit is configured in such as way that the recording process is initiated by a switching impulse initiated by the user. Activation occurs when the switch button 3 is pressed for a prescribed minimum duration of, for example, 3 seconds.

The data processing unit is configured in such a way that it starts recording or saves data when the acquired respiratory flow signal fulfils a certain criterion, e.g. a predefined periodicity criterion.

The detection appliance 1 exhibits a first pressure measurement connection 4 to which can be connected a measurement cannula 5.

As shown in FIG. 1b, this measurement cannula 5 can be connected to a nasal pressure measurement spectacle device 6 for registering a back-pressure event in the respiratory gas flow out of the nasal openings 7a, 7b.

It is possible to equip the detection appliance 1 with a second pressure measurement connection for acquiring a second pressure measurement signal. The ability to acquire two pressure measurement signals makes it possible to operate the detection appliance 1 in such a way that it can separately acquire the respiratory flow signals from the left and right nasal openings 7a, 7b respectively.

FIG. 1c shows a further variation for generating a signal that is indicative of the respiratory gas flow. This variation comprises a mask 17 designed in the style of a mouth protection and made from a gas-permeable material (e.g. unidirectional filter made from paper material). This mask 17 makes it possible to produce, in the immediate area surrounding the mouth and nasal opening, a pressure difference relative to the ambient level. This pressure difference is determined in particular by the air tightness of the mouth protection and the permeability of the mask or filter material. Any non-linearities that may exist can be determined and compensated for within the detection appliance.

The mask interior defined by this mouth protection which acts as a diaphragm is connected to the detection appliance via the measurement cannula 5. It is possible to provide the mask with flap or valve devices 18, 19 that facilitate the inhalation process. These valve or flap devices, in particular the degree in which they are open, can also be used to acquire signals that are indicative of the respiration. The signal transmission can occur by wireless means, in particular optically for example using infrared light.

The signal that is indicative of the respiratory gas flow can also be acquired by means of other measurement equipment, in particular measurement diaphragms or volumetric flow sensors.

The detection appliance 1 can provide a device 8 for detecting chest expansion. As shown in FIG. 1d, the facility for detecting chest expansion may comprise a strap element 9 that can be fitted around the chest area of the user 10. It is possible to design this strap element 9 in such a way that a signal that is indicative of the extension of the strap, or the load on the strap can be derived from it. It is also possible to provide the detection appliance 1 with a means of detecting the load on the strap. In particular, it is possible to provide the detection appliance 1 with a loop feature 12 by means of which the extension of the strap, or the forces on the strap can be detected. It is also possible to provide the detection appliance 1 with pressure or force detection structures 8 by means of which the force exerted by the strap located on top of these force detection structures can be detected. The strap 9 for detecting the chest expansion can also serve to fasten the detection appliance 1 to the user. It is also possible to use the chest strap only for fastening the detection appliance 1 and not for detecting the chest expansion.

The detection appliance 1 can be provided with electrode devices through which the ECG signals from the user can be acquired by locating the detection appliance directly onto the skin of the user. These ECG signals can also be recorded with temporal information.

The recording process can be initiated by the user by means of the switch button 3. It is also possible to configure the detection appliance 1 in such a way that the recording process is ended as a result of the fulfilment of a time criterion. In particular, it is possible to end the recording process when it has reached a prescribed duration of, for example, 9.5 h.

The recording process is also ended under switch control if the acquired respiratory flow signal fulfils a certain switch-off criterion within a certain switch-off time window.

The detection appliance 1 is provided with an interface device 14 for transmitting the recorded data to an external analysis system. Here this interface device is implemented as a USB interface. The detection appliance also comprises an infrared interface for potential-free signal acquisition. The generated signals relating to the respiration that are obtained can be extracted for further analysis via this infrared interface while the appliance is in operation. The detection appliance 1 can thus be operated as a measurement transducer.

It is also possible to design the detection appliance 1 in such a way that the memory device is incorporated in the detection appliance 1 in a replaceable manner or can be attached thereto. Such a memory device can be in the form of a card or, in particular, a USB flash stick. By first creating an entry in the memory device, it is possible to record personal data on the storage medium. On the basis of this initial recording, it is possible to pre-configure the detection appliance 1 or ensure that the acquired data is correctly assigned to the specific user.

The configuration of the data processing unit is set by a data processing program, where this data processing program is in preference modifiable or substitutable. The reproduction of the data processing program in the detection appliance 1 can occur via a ROM device or a RAM device, in particular via the previously mentioned interface device 14, additional interface devices or the storage medium.

Along with the in preference intuitive and easy-to-use switch device 3, the detection appliance 1 is also provided with indicator devices 15 for indicating the operational readiness or the functional state of the detection appliance. In the embodiment shown, the recording readiness of the detection appliance is indicated by the periodic blinking of a green signal diode.

The detection appliance 1 comprises a power supplying device which in this case takes the form of a battery unit. The battery unit is in a compact form so that the detection appliance can be designed to be flat and miniature and possess little weight.

The data processing unit is coupled to a calibration device for calibrating the respiratory flow signal. The calibration device is designed in such a way that it can perform an automatic adjustment of the system to the acquired signal level.

FIG. 1e shows a sketch illustrating a second form of embodiment of an inventive concept for separately registering signals that are indicative of nasal respiration and oral respiration respectively. These signals can be acquired as pressure signals via measurement cannulae. The signals can, in particular, be obtained as a pressure difference signal indicating the pressure difference relative to ambient pressure. The signals can be normalized and edited by means of signal processing procedures. The edited signals can be used to describe and, in particular, visualize the temporal course of the respiration.

FIG. 1f shows a sketch illustrating a concept for monitoring respiration by registering signals X1, X2, X3 that are indicative of the respiratory gas flow through the left nasal opening, the right nasal opening and the mouth of the user respectively. These signals can, in particular, be registered via pressure measurement cannulae. The signals X1, X2 can, for example, be collected as back-pressure signals using a nasal spectacle device. The signal X3 can be acquired using a measurement cannula inserted in the flow area in the region of the upper lip of the user where gas exchange occurs during oral respiration. It is possible to collectively evaluate the signals X1, X2, X3 in such a way that the sum of the signals fulfils a plausibility criterion, for example with regard to the tidal volume.

FIG. 1g shows a sketch detailing an acquisition device for application to the nose with an integrated facility for detecting the oral respiration. The registration device comprises a base body 30 produced from an elastomeric material, in particular silicone rubber. The base body defines an enclosed measurement space that includes the nose tip area 31 of the user and incorporates the nasal openings. This enclosed measurement space is connected to the surroundings via a measuring diaphragm device 32. The measuring diaphragm device is designed in such a way that it provides a relative low, but defined flow resistance between the enclosed measurement space and the surroundings when respiratory gas is displaced. The pressure differences arising in the enclosed measurement space relative to the surroundings as a result of the flow resistance of the measuring diaphragm device can be registered via the measurement cannulae 5 and converted to obtain data that is indicative of the nasal respiration.

The base body 30 is provided with a sensor device 33 for registering an event that is indicative of oral respiration, in particular, a pressure fluctuation. This pressure fluctuation can also be transported for further recording via a measurement channel or other signal transmission device. The application of the measurement device provided for registering oral respiration to the structure sitting on the nose of the user guarantees an especially advantageous, in particular positionally stable and reproducible arrangement of this measurement device.

The measuring diaphragm 32 can take the form of a mesh, screen or even woven fabric element. As later remarked in connection with FIG. 1n, it is possible to purge the enclosed measurement space by supplying a breathable gas, in particular ambient air. This makes it possible to ensure an adequate exchange of air even when respiration is particularly shallow. It is also possible to shift the pressure signal registered via the cannulae 5 into the positive region when the respiration is shallow. An under-pressure will then only arise when the inspiration flow is greater than the purging flow.

FIG. 1h shows a sketch for acquiring a signal representing combined nasal and oral respiration using a mask device 35 covering the nose and mouth regions. The mask device can be produced from an air-permeable material or, as shown here, provided with a flap or measuring diaphragm device 32.

FIG. 1i illustrates an acquisition device for registering a signal indicative of nasal respiration. Similar to the 29 variant according to FIG. 1g, this registration device comprises a base body 30 that defines an enclosed measurement space incorporating the tip of the nose. The base body 30 is produced from a plastic material, in preference a transparent elastomeric material.

The base body 30 comprises a mounting ridge 36 following the bridge of the nose. The mounting ridge 36 has been provided with mounting wings 37. The mounting ridge 36 and the mounting wings 37 can be fixed in place on the user by means of adhesive strips or, if necessary, can be designed to be self-adhesive in specific areas. Flexible inserts, in particular wire segments can be incorporated into the mounting ridge 36 and/or mounting wings 37 allowing the acquisition device to be adapted to the particular nasal structure of the user.

The base body 30 defines an air exit section 38 through which a displacement of respiratory gas from/to the nasal air passages and the surroundings can occur. The air exit section 38 can be designed so as to provide a defined flow resistance so that a signal based on the prevailing pressure in the enclosed measurement space and indicative of the respiration can be acquired, e.g. via the cannula 5 shown here.

The base body 30 can be designed in such a way, in particular in the area adjacent to the nasal openings when in the applied position, that an especially advantageous acquisition of the nasal respiratory gas flow is possible. An especially suitable construction is sketched in FIG. 1j.

It is not essential for the base body 30 to be produced from plastic material. It is also possible to produce it from paper, cellulose, fibre or other materials, in particular those suitable for once-off use. Sections of the interior of the base body can be provided with foam material or other padding material in order to achieve airtightness or padding, in particular in the nose bridge area.

The base body 30 presented in cross-section and in a simplified manner in FIG. 1j is provided with a sealing lip structure 40 which seals off the enclosed measurement space from the surroundings.

The enclosed measurement space contains an air-guiding structure that sits on the nose of the user in the area surrounding the nasal openings. In this embodiment example, the air-guiding structure is designed in such a way that it allows separate signals for the left and right nasal flow to be collected.

The air-guiding structure comprises a baffle 41 that diverts the air flowing through the nasal openings. A pressure measurement port 42 is provided in a typical back-pressure location of the diversion path created by the baffle. The pressure prevailing in each of the pressure measurement ports can be acquired via a measurement cannula 5.

The base body 30 shown here in cross-section has been produced from an elastomeric material. Elastic insertion channels 43 are provided in the area of each pressure measurement port into which can be inserted a plug-in connector 44 for attaching the respective cannula 5.

The diversion path is designed in such a way that it diverts the air flow by about 180°. Each pressure measurement port 42 is located in the area where diversion occurs.

The baffle 41 can be designed in such a way that is elastically flexible and provides a passage of larger cross-sectional area at higher respiratory gas flow rates. It is also possible to detect the respiratory gas flow based on the deflection of the baffle. To avoid blockage of the pressure measurement port 42, it is possible to introduce a purging air flow, either permanently or intermittently, into the measurement cannula 5.

FIG. 1k shows an acquisition device with acquisition elements 50 introduced into each of the nasal openings and fastened by means of a ridge 36 resting on the bridge of the nose. The acquisition elements 50 are produced from an elastomeric material and contoured in such a way that they can be applied to the nasal opening area of the user in an advantageous manner. The acquisition elements form measurement channel sections through which it is possible to acquire the nasal respiratory gas flow. It is possible to introduce the measurement channel section into a measurement diaphragm or flap device 32 with the aid of which a defined flow resistance or a flow effect advantageous to the signal collection can be obtained.

FIG. 1l shows an acquisition element with two elastic connector pieces 51, 52 that can be introduced in each respective nasal opening, and an axial support providing base section 53. In this embodiment example, both connector sections 51, 52 open out into a common measurement channel section 54 which in turn opens out into the surroundings via a measurement diaphragm.

FIG. 1m, which is in the form of a simplified cross-sectional sketch, shows a further variation of a device for acquiring signals that are indicative of the nasal respiratory gas flow. In this embodiment example, the connection sections 51, 52 are provided with bellow structures 51a, 51b.

The acquisition device forms two measurement channels 55, 56 that are in connection with the surroundings via diaphragm or flap elements 57, 58. The flap elements 57, 58 are set into a circumferential groove located in the opening region of each measurement channel 55, 56.

Acquisition of each respective pressure signal in the region of the measurement channels occurs via the pressure measurement port sections 59, 60.

The signal collection can, as previously described, occur via a cannula 5 or a directly connectable or insertable measuring transducer 61. A signal that is indicative of the pressure in the respective measurement channel can be converted to an electrical or optical signal by means of the measurement transducer 61.

FIG. 1n shows, in sketch form, a measuring arrangement in which purging air is actively introduced into an enclosed measurement space defined by an acquisition device. To this purpose, a purging-air line 70 has been provided that opens into the enclosed measurement space. The purging air can be supplied via a fan device or, in preference, via a static pumping device, e.g. gear pump or other volumetric pumping device F.

The air displacement occurring between the enclosed measurement space and the surroundings can be detected by means of a pneumotachograph 71 and recorded for further analysis by the detection appliance 1. The thereby produced offset of the respiratory gas flow signal can be taken into consideration in the analysis procedure. The purging-air line 70 can have a small cross-section of, for example, 10 mm$^2$. The purging volume can vary within the range of 1 to 5 l/min.

FIG. 2 shows a variation of the detection appliance 1 exhibiting a structural component 20 that is compatible to a playback unit 21 whose construction corresponds to that of a Game Boy. The detection appliance is thereby designed in such a way that at least one portion of it can be introduced into the insertion slot 22 of a Game Boy.

The detection appliance 1 is designed in such a way that it comprises a base module 23 to which a recording transfer module 20 can be coupled.

This recording transfer module 20 is designed as a Game Boy compatible structure. This enables the recorded data to be visualized via an intuitive, simply-to-understand user interface on a conventional end-user device 21 and, if necessary, to be analysed and processed with regard to selected properties. This makes it possible, in particular, to output a summary result in the form of a severity bar 28. This bar chart clearly indicates whether —and to what extent—a treatment-relevant disorder is present, or not.

The supply of power, and the conversion of the pressure signal acquired from the user via the cannula 5, occurs in preference in the base module 23. To this end, the base module 23 comprises a battery compartment and a pressure sensor as well as a switch device 24.

The recording module 20 comprises a data processing unit that is configured in such a way that it records onto a memory device data that is indicative of the temporal course of the breathing. The recording module 20 can be provided with an interface device 14 for reading the recorded data. It is possible to connect the memory device 25 to the recording module 20 in a detachable manner so that is possible to separate the memory device 25 from the recording module and introduce it into another system for further analysis and visualization.

The acquisition of the respiratory signal can, as an alternative to acquisition using a nasal cannulation arrangement 5, also occur by means of other measuring equipment.

Using the previously stated detection appliance 1, it is possible to obtain an evaluation result that is based on the measurement signals associated with the breathing of the person and which is indicative of the physiological state of the user, whereby evaluation characteristics are generated from said measurement signals through the use of standardized analysis systems and a least one evaluation result is generated from a result generation step based thereon that indicates the severity of any illness present according to prescribed evaluation criteria, in particular through visualization, for example, in the form of a bar chart.

The entire captured data can be input to further evaluation procedures and, as depicted in FIG. 3, graphically visualized via a convenient menu interface.

The inventive detection appliance, and the signal processing method that can be performed therewith, provide an advantageous means of creating a quantity of data from the signal collection carried out at home by the user over a continuous period of approx. 6 to 8 hours based on which evaluation characteristics can be generated from which can be produced reliable evaluation results obtained in a standardized repeatable manner that can in an advantageous manner form the basis of a subsequent diagnosis and thereby contribute to a standardized evaluation.

Further particulars, in particular relating to the classification and automated evaluation of the respiration, can be found in the description that follows.

The breath 100 depicted in FIG. 4a relating to the temporal course of the respiratory gas flow comprises an inspiratory phase I and an expiratory phase E. The determination of the respiratory phase boundary G between the inspiratory phase and the expiratory phase occurs by means of simultaneous analysis of several curve tracing criteria, in particular taking into consideration the currently prevailing respiratory pattern and the peak values of the respiratory gas flow and pattern, the determined tidal volume, and taking into consideration the respiratory phase periods of preceding breaths.

The respiratory gas flow trace depicted in FIG. 4a describes the change in respiratory flow over time for a single unimpaired breath. The breath can be evaluated on the basis of temporal relationships, e.g. of the inspiration and expiration time to one another, or other properties, e.g. the total breath duration. In an especially advantageous embodiment of the invention, the quotient of the inspiration time and the total breath duration is calculated in order to recognize changes in the breathing.

FIG. 4b depicts the changes in respiratory gas flow over a longer time frame. As is evident in the diagram, the individual breaths vary in particular with respect to the minima and maxima that occur. The horizontal line 200 drawn on the diagram illustrates the statistically most probable maximum respiratory flow occurring in the inspiratory phases. A statistical analysis can also be performed on the inspiration time, expiration time and total breath duration over several breaths (in preference 10 breaths).

FIG. 4c depicts the temporal course of a signal that is indicative of the respiratory gas pressure and in which the signal exhibits oscillation sequences 300a, 300b, 300c, 300d and 300e caused by snoring. The pressure fluctuations caused by snoring can be captured via a pressure detection device located close to the user, for example, a respiratory-gas pressure measurement hose. It is possible to capture such pressure fluctuations via a microphone unit.

FIG. 4d shows the temporal course of the respiratory gas flow for several breaths 100 that are interrupted by a period of breathing cessation 500. The period of breathing cessation 500 detected on the basis of the respiratory gas flow exhibits a duration that exceeds a predefined limit value of, for example, 20 seconds and is therefore classified as an apnoea phase. Both the breaths detected before the period of breathing cessation 500 in this diagram and those that follow it show flow-limitation characteristics that are recorded and associated with the relevant breath.

FIG. 5 shows a temporal course of the breathing gas flow that contains a hypopnea phase 600. A hypopnea phase 600 is considered to be present when three breaths 1 that are classified as normal are followed by at least two but at most three breaths whose volume differential relative to the three preceding breaths exceeds a prescribed limit 30 value.

FIG. 6 shows a temporal course of the respiratory gas flow over several breaths where the first 4 visible breaths 100 show flow-limitation characteristics. These flow-limitation characteristics are recognizable in the displayed course of the respiratory gas flow on account of the plateau 700 shapes therein and the presence of several local maxima 800. In the displayed breaths, the flow-limitation characteristics occur, in each case, in the inspiratory phase of the relevant breaths 100. The first 4 breaths 100 displayed here are followed by three further, in part, flow-limited breaths 140 that can be associated with a hypopnea phase and which, in part, also display flow-limitation characteristics.

FIG. 7 shows the temporal course of the respiratory gas flow for a respiration period classified as stable. The flow of respiratory gas, the breathing frequency, the amplitude and breathing pattern of the respiratory gas flow are regular within a prescribed region that can be defined by means of a time range or a given number of breaths. The breathing stability in the respiratory gas flow history displayed here lies above the breathing stability limit value of 0.86. A statistical analysis can also be performed on the inspiration time, expiration time and total breath duration over several breaths (in preference 10 breaths). In the phase of stable respiration shown here, no respiratory disturbances (OSA) are evident.

FIG. 8 shows a temporal course of the respiratory gas flow over several breaths where the respiratory flow is irregular during the time period shown and in which respiratory disturbances (OSA) are evident for particular breaths. A statistical analysis can also be performed on the inspiration time, expiration time and total breath duration over several breaths (in preference 10 breaths). In the implementation example shown here, the breathing stability index lies under a limit value of, in preference, 0.911.

FIG. 9 shows a temporal course of the respiratory gas flow in relation to a respiratory-gas pressure signal. The respiratory-gas pressure signal contains phases of high-frequency oscillations which, in the present example, can be associated with inspiratory snoring.

The invention claimed is:

1. A mobile detection appliance configured to record and evaluate data indicative of a respiratory condition of a user, the mobile detection appliance comprising:
   a sensor configured to generate a respiratory flow signal based on at least one of an expiratory gas flow and an inspiratory gas flow received from a patient interface, the respiratory flow signal being indicative of the user's respiratory gas flow;
   a chest strap having (a) an adjacent surface serving in part as a user-contact surface when worn by the user and (b) a non-adjacent surface that is opposite the user-contact surface;
   an electronic data processing unit which comprises a memory device and is configured to process the generated respiratory flow signal and a chest expansion signal generated using the chest strap, said electronic data processing unit being configured to store data that is indicative of a temporal course of the generated signals when the generated signals fulfill a certain criterion; and
   a common housing with a port configured to receive said at least one of the expiratory gas flow and the inspiratory gas flow from the patient interface, wherein the common housing houses the sensor and the data processing unit, the common housing being selectively fastenable to the user so that the sensor and the data processing unit are securable as a unit to the user,
   wherein the common housing comprises a first exterior surface and a second exterior surface, the first exterior surface being opposite the second exterior surface, and
   wherein the first exterior surface is configured to be in contact with a body of a user when in use, and wherein the second exterior surface is configured to be faced away from the body of the user and to be in contact with the adjacent surface of the chest strap so that the adjacent surface lies over the second exterior surface to retain the common housing against the user when in use, and wherein the second exterior surface includes at least one detector, the at least one detector comprising a pressure or force sensor and configured to be in contact with the adjacent surface of the chest strap to detect force exerted by the chest strap upon the at least one detector to generate the chest expansion signal when in use.

2. A mobile detection appliance according to claim 1, wherein the data processing unit is configured to check whether the generated respiratory flow signal fulfils prescribed signal quality criteria.

3. A mobile detection appliance according to claim 1, wherein the data processing unit comprises a time-keeping device and data that is indicative of the respiratory flow signal is recorded in conjunction with time information.

4. A mobile detection appliance according to claim 1, wherein the data processing unit is provided with a data compression system.

5. A mobile detection appliance according to claim 1, wherein the data processing unit is configured such that storage of the data is initiated by a switching impulse triggered by the user.

6. A mobile detection appliance according to claim 1, wherein the data processing unit is configured to suppress storage of the data when the generated respiratory flow signal does not fulfill the certain criterion.

7. A mobile detection appliance according to claim 1, wherein the common housing further comprises a first pressure measurement connection at the port to that is connectable to a measurement cannula.

8. A mobile detection appliance according to claim 7, wherein the common housing further comprises a second pressure measurement connection configured to acquire a second pressure measurement signal.

9. A mobile detection appliance according to claim 1, wherein said sensor is configured to generate separate respiratory flow signals that are indicative of left and right nasal openings, respectively.

10. A mobile detection appliance according to claim 1, wherein the certain criterion comprises a predetermined periodicity criterion.

11. A mobile detection appliance according to claim 1, wherein the data processing unit is configured to perform a data entry indicative of a time location when the respiratory flow signal does not fulfill certain criteria.

12. A mobile detection appliance according to claim 1, wherein the data processing unit is configured to suppress recording of the generated respiratory flow signal and instead store data indicative of a time location when the generated respiratory flow signal does not fulfill the certain criterion.

13. A mobile detection appliance according to claim 1, wherein the common housing comprises a first loop feature projecting from the second exterior surface, the first loop feature configured to accept the chest strap and arranged to align the chest strap in a position over the at least one detector of the second exterior surface.

14. A mobile detection appliance according to claim 13, wherein common housing comprises a second loop feature projecting from the second exterior surface, the second loop feature configured to accept the chest strap and arranged to align the chest strap in the position over the at least one detector of the second exterior surface, the position over the at least one detector being between the first loop feature and the second loop feature.

15. A mobile detection appliance according to claim 14, wherein the second exterior surface comprises an additional detector comprising a pressure or force sensor and configured to be in contact with the adjacent surface of the chest strap to detect force exerted by the chest strap upon the at least one detector to generate a further chest expansion signal when in use.

16. A mobile detection appliance according to claim 1, wherein the data processing unit is configured to transmit the data that is stored to an external analysis system.

17. A mobile detection system comprising:
the mobile detection appliance of claim 1; and
the patient interface, the patient interface being configured to engage the user's face and receive at least one of the expiratory gas flow from the user and the inspiratory gas flow from ambient gas.

18. A mobile detection device according to claim 1, wherein the first exterior surface of the common housing comprises electrode devices to directly contact skin of the user, the electrode devices configured to provide ECG signals from the user.

19. A mobile detection device according to claim 1, wherein the data processing unit is configured to generate evaluation characteristics based on the respiratory flow signal and the chest expansion signal, and wherein the evaluation characteristics are subjected to an associative analysis.

20. A mobile detection device according to claim 1, wherein the sensor is in fluid communication with the port.

21. Method for acquiring and evaluating measurement signals while a user is asleep, the measurement signals being indicative of a respiratory condition of the user, comprising:
providing a chest expansion monitor for use with a chest strap, the chest strap having (a) an adjacent surface serving in part as a user-contact surface when worn by the user and (b) a non-adjacent surface that is opposite the user-contact surface, (b) a sensor and (c) an electronic data processing unit to the user,
wherein the chest expansion monitor, the sensor and the electronic data processing unit are commonly housed within a common housing of a mobile detection appliance so that the chest expansion monitor, the sensor and the electronic data processing unit are securable to the user as a unit;
providing at least one of an expiratory gas flow from the user and an inspiratory gas flow from ambient gas to the sensor that is commonly housed within the mobile detection appliance;
providing chest expansion signals to the chest expansion monitor, the chest expansion signals being indicative of an expansion of the user's chest;
generating the measurement signals within the mobile detection appliance based on the chest expansion signals and at least one of the expiratory gas flow and the inspiratory gas flow;
generating evaluation characteristics from said measurement signals through use of several analysis systems; and
generating at least one evaluation result from a result generation step based thereon in which the evaluation characteristics are subjected to an associative analysis, wherein said measurement signals are acquired by the data processing unit in a course of a signal acquisition phase preceding the associative analysis and stored when they fulfill a certain criterion, wherein the common housing comprises a first exterior surface and a second exterior surface, the first exterior surface being opposite the second exterior surface, and wherein the first exterior surface is configured to be in contact with a body of a user when in use, and wherein the second exterior surface is configured to be faced away from the body of the user and to be in contact with the adjacent surface of the chest strap so that the adjacent surface lies over the second exterior surface to retain the common housing against the user when in use, and wherein the second exterior surface includes at least one detector, the at least one detector comprising a pressure or force sensor and configured to be in contact with the adjacent surface of the chest strap to detect force exerted by the chest strap upon the at least one detector to generate the chest expansion signal when in use.

22. Method according to claim 21, wherein apnea indicators are included among the evaluation characteristics.

23. Method according to claim 21, wherein hypopnea indicators are included among the evaluation characteristics.

24. Method according to claim 21, wherein flow limitation indicators are included among the evaluation characteristics.

25. Method according to claim 21, wherein a contributing characteristic predominantly included among the evaluation characteristics is generated within a generation time window that is smaller than an association time window used in the associative analysis.

26. Method according to claim 21, wherein a physiological characterization of the user according to obstructive, central and/or mixed respiratory disorders occurs on a basis of the associative analysis.

27. Method according to claim 21, wherein the evaluation characteristics are generated on a basis of breathing stability criteria.

28. Method according to claim 21, wherein the evaluation characteristics are generated on a basis of statistical analysis procedures.

29. Method according to claim 21, wherein the evaluation characteristics are generated as an array of characteristics.

30. Method according to claim 21, wherein an evaluation characteristic is generated from a duration of normal respiration phases and/or normal respiration characterizing features and/or features representing a duration of regular or irregular respiration phases and/or regular and/or irregular features.

31. A method according to claim 21, further comprising:
classifying said acquired measurement signals as invalid when said acquired measurement signals do not fulfill the certain criterion;
suppressing storage of the acquired measurement signals that are classified as invalid; and
storing data indicative of time locations associated with respective invalid measurement signals.

32. A method according to claim 21, wherein the sensor and the electronic data processing unit are commonly housed within a housing of the mobile detection appliance, and wherein said at least one of the expiratory gas flow from the user and the inspiratory gas flow from ambient gas is provided to the sensor by way of a port in the housing of the mobile detection appliance.

* * * * *